(12) United States Patent
Khorzad et al.

(10) Patent No.: US 6,746,652 B2
(45) Date of Patent: Jun. 8, 2004

(54) PRODUCTION OF HYDROGEN PEROXIDE VAPOR-AIR MIXTURES

(75) Inventors: Davoud Khorzad, Lake Forest, IL (US); Robert J. Thrash, St. Charles, IL (US); Jimmy Fisher, Hawthorn Woods, IL (US); Thomas F. Cullen, Des Plaines, IL (US)

(73) Assignee: Pharmaceutical Systems, Inc., Mundelein, IL (US)

( * ) Notice: Subject to any disclaimer, the term of this patent is extended or adjusted under 35 U.S.C. 154(b) by 506 days.

(21) Appl. No.: 09/901,337

(22) Filed: Jul. 9, 2001

(65) Prior Publication Data

US 2003/0007916 A1 Jan. 9, 2003

(51) Int. Cl.[7] .............................. A61L 9/00; B01J 7/00
(52) U.S. Cl. ........................ 422/305; 422/28; 422/29; 422/123; 422/306
(58) Field of Search ..................... 422/305, 28, 29, 422/33, 306, 123

(56) References Cited

U.S. PATENT DOCUMENTS

| | | |
|---|---|---|
| 4,296,068 A | 10/1981 | Hoshino |
| 4,366,125 A | 12/1982 | Kodera et al. |
| 4,680,163 A | 7/1987 | Blidschun et al. |
| 4,707,334 A | 11/1987 | Gerhard |
| 4,742,667 A | 5/1988 | Muller et al. |
| 4,797,255 A | 1/1989 | Hatanaka et al. |
| 4,992,247 A | 2/1991 | Foti |
| 5,007,232 A | 4/1991 | Caudill |
| 5,078,976 A | 1/1992 | Shibauchi et al. |
| 5,152,968 A | 10/1992 | Foti et al. |
| 5,178,841 A | 1/1993 | Vokins et al. |
| 5,258,162 A * | 11/1993 | Andersson et al. ........... 422/28 |
| 5,482,684 A | 1/1996 | Martens et al. |
| 5,525,295 A | 6/1996 | Pflug et al. |
| 5,620,656 A | 4/1997 | Wensky et al. |
| 6,096,265 A | 8/2000 | Mezger et al. |
| 6,406,666 B1 * | 6/2002 | Cicha et al. ................. 422/28 |

FOREIGN PATENT DOCUMENTS

| | | |
|---|---|---|
| GB | 1582060 | 12/1980 |
| GB | 2089213 | 6/1982 |

OTHER PUBLICATIONS

International "Written Opinion" for PCT Application Ser. No. PCT/US02/21501, mailed Jun. 5, 2003.
International Search Report for PCT Application Ser. No. PCT/US02/21500, mailed Nov. 5, 2002.

* cited by examiner

*Primary Examiner*—Krisanne Thornton
(74) *Attorney, Agent, or Firm*—Stephen P. Gilbert, Esq.; Bryan Cave LLP

(57) ABSTRACT

Apparatus and method for producing at high efficiency vaporization a precisely controllable, continuously adjustable gas-phase flow of a vaporizable liquid (e.g., hydrogen peroxide) in a carrier gas (e.g., air) are disclosed. The gas-phase product flow can be substantially continuous, low-temperature, unsaturated with respect to the vaporized vaporizable liquid, and of substantially constant vaporized vaporizable liquid concentration as a function of time. Fine particles of the vaporizable liquid are produced and introduced into the flow of carrier gas/vapor in a vaporization plenum with a sufficient flow of carrier gas/vapor to provide a curtain of carrier gas/vapor between substantially all of the fine particles of vaporizable liquid and the inner surface of the vaporization plenum.

32 Claims, 3 Drawing Sheets

PRODUCTION OF HYDROGEN PEROXIDE VAPOR-AIR MIXTURES

BACKGROUND OF THE INVENTION

1. Technical Field

Figure 1:
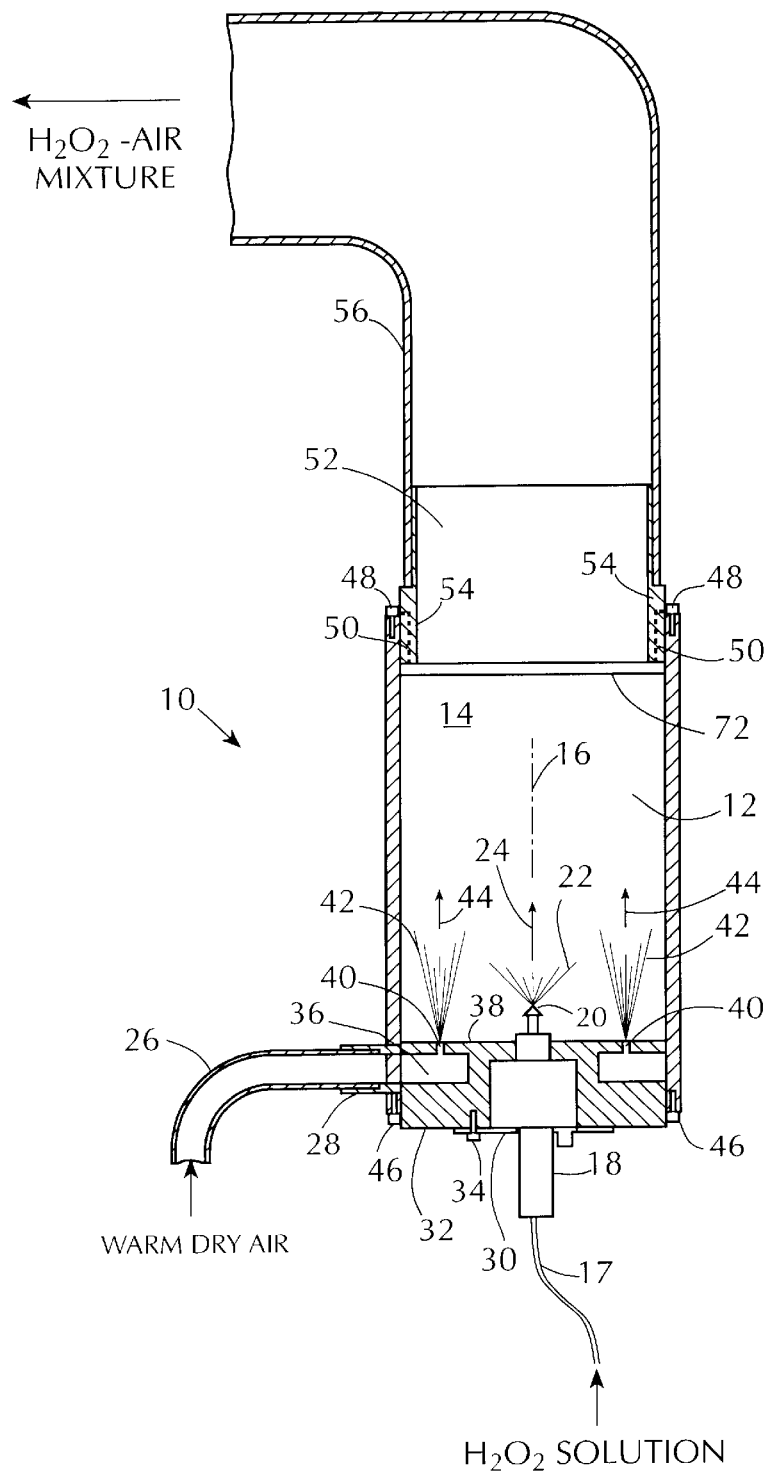
Figure 2:
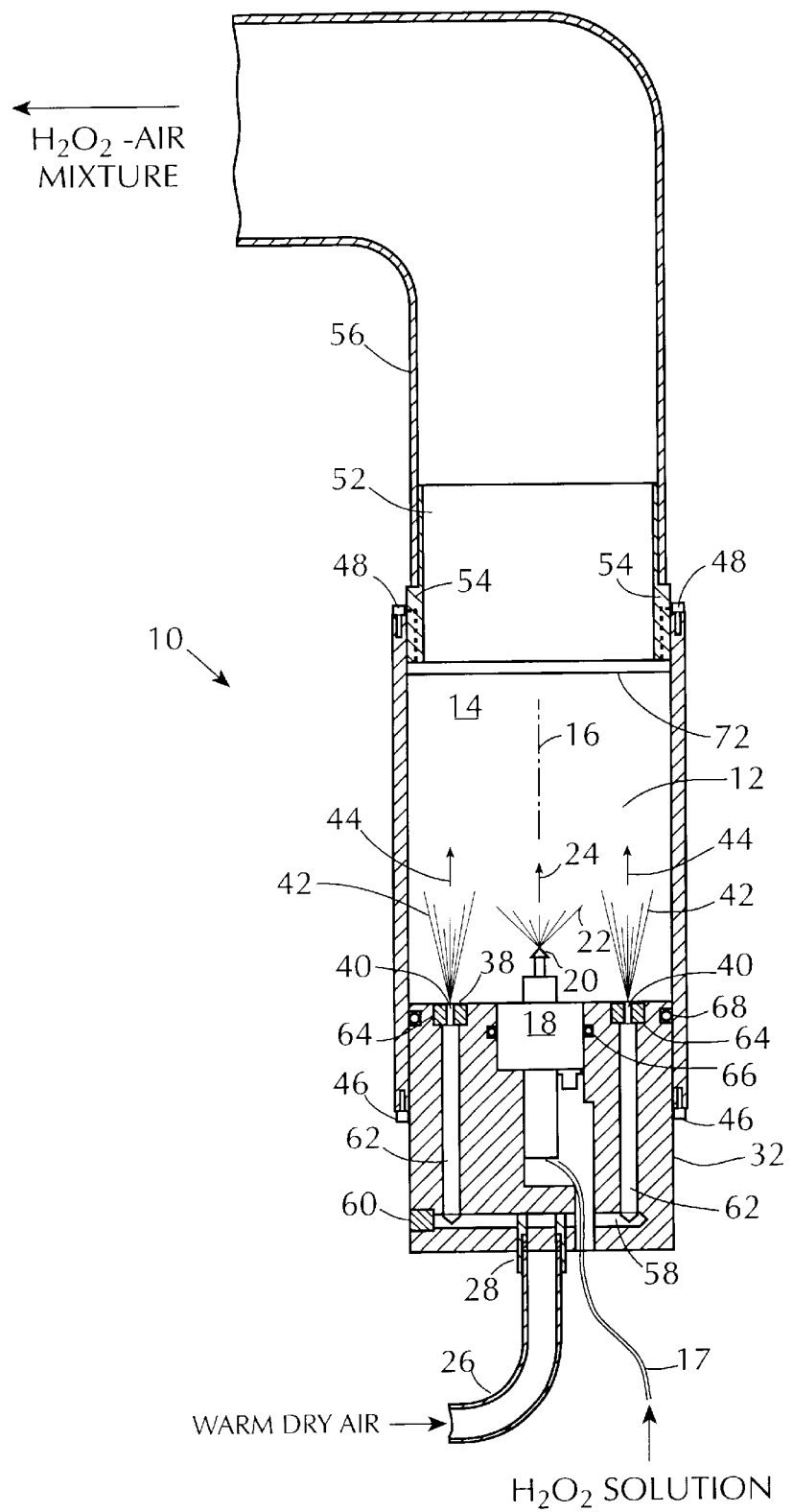

This invention concerns the production of hydrogen peroxide vapor and, more specifically, hydrogen peroxide vapor-air mixtures.

2. Background Art

Hydrogen peroxide is used in connection with bleaching, sterilization, and other processes. In particular, for hydrogen peroxide sterilization processes, it is known to break the hydrogen peroxide liquid into particles, e.g., to facilitate subsequent vaporization. See, e.g., U.S. Pat. Nos. 4,296,068, 4,366,125, 4,680,163, 4,707,334, 4,797,255, 4,992,247, 5,152,968, 5,525,295 and British Patent Documents GB 1,582,060 and GB 2,089,213. In U.S. Pat. No. 6,096,265, a film of hydrogen peroxide formed on a porous member is heated to vaporize the hydrogen peroxide, after which the vaporized hydrogen peroxide is mixed with air. (All of the foregoing documents, as well as all other documents cited or otherwise referenced herein, are incorporated herein in their entireties for all purposes.)

For sterilization processes utilizing vaporized hydrogen peroxide, the hydrogen peroxide vapor is often produced by allowing drops of aqueous liquid hydrogen peroxide solution (e.g., 1 to 3 millimeters in diameter) to contact a hot solid surface. See, e.g., U.S. Pat. No. 4,797,255. It is also known to break the hydrogen peroxide liquid into finer particles or a mist. See, e.g., U.S. Pat. Nos. 4,296,068, 4,366,125, 4,680,163, 4,707,334, 4,992,247, 5,152,968, 5,525,295 and British Patent Documents GB 1,582,060 and GB 2,089,213. In some cases, an atomizer (see, e.g., U.S. Pat. No. 5,525,295) or an ultrasonic device (see, e.g., U.S. Pat. Nos. 4,296,068, 4,366,125, 4,680,163, 4,707,334, 4,992,247, and 5,152,968 and British Patent Documents GB 1,582,060 and GB 2,089,213) is used to produce the fine particles or mist.

In some cases, hot air vaporizes the fine particles of hydrogen peroxide to create a hydrogen peroxide vapor-air mixture (see, e.g., U.S. Pat. Nos. 4,992,247 and 5,152,968 and British Patent Document GB 1,582,060); however, the processes of those patents utilize high volumetric air velocity and/or high temperature (i.e., at least 200° F., which is over 93° C.), even to the point of boiling the hydrogen peroxide particles, and/or can produce only saturated hydrogen peroxide vapor-air mixtures (i.e., the only mixtures that can be produced are those that are saturated with hydrogen peroxide).

Hydrogen peroxide decomposes in the vapor phase (the stabilizers that help prevent its decomposition in aqueous liquid solution do not function in the vapor phase). Thus, for hydrogen peroxide vapor phase sterilization, in which the hydrogen peroxide concentration must be maintained above a predetermined minimum, the hydrogen peroxide vapor is typically produced in "real time" (i.e., as it is needed) so that it can be contacted with the articles to be sterilized before decomposition has reduced the concentration below the predetermined minimum. However, because of the significantly different vapor pressures of hydrogen peroxide and water, an ever present problem when producing hydrogen peroxide vapor from aqueous liquid hydrogen peroxide solution is producing a substantially constant concentration of hydrogen peroxide in the vapor phase mixture as a function of time, because differential vaporization may occur.

Thus, the need remains for an apparatus and a method for producing hydrogen peroxide vapor-air mixtures that have a substantially constant concentration of hydrogen peroxide as a function of time and that need not be saturated with the hydrogen peroxide. The need also remains for apparatus and method that allow the production of such mixtures at low air flow rates and at low temperature and whose flow are substantially continuous (e.g., non-pulsating). The need also exists for producing such mixtures that use other carriers (i.e., instead of air) and/or other vaporizable liquids (i.e., instead of hydrogen peroxide).

SUMMARY OF THE INVENTION

Method and apparatus that satisfy those needs and provide still other benefits that will be apparent to one skilled in the art have now been invented. Broadly, in one aspect, the invention concerns an apparatus that can produce at high vaporization efficiency from air and an aqueous liquid solution of hydrogen peroxide a substantially continuous flow of a low-temperature unsaturated gas-phase mixture of air and vaporized hydrogen peroxide of substantially constant hydrogen peroxide concentration as a function of time, said apparatus comprising:

(a) a vaporization plenum having an inner surface;

(b) means for breaking the aqueous liquid solution of hydrogen peroxide into fine particles and for flowing the fine particles in the vaporization plenum, the bulk flow of the fine particles flowing in the vaporization plenum being in a first direction;

(c) means for flowing the air in the vaporization plenum and for flowing at least some of the air between the inner surface of the vaporization plenum and substantially all of the fine particles to create a curtain of air between the inner surface of the vaporization plenum and substantially all of the fine particles, the bulk flow of the air in the vaporization plenum flowing in substantially the same direction as the first direction; and (d) means for causing substantially all of the fine particles to vaporize in the flow of the air to produce a flow of a gas-phase mixture of air and vaporized hydrogen peroxide of substantially constant hydrogen peroxide concentration as a function of time.

In another aspect, the invention concerns a method for producing at high vaporization efficiency from air and an aqueous liquid solution of hydrogen peroxide a flow of a gas-phase mixture of air and vaporized hydrogen peroxide of substantially constant hydrogen peroxide concentration as a function of time, said method comprising:

(a) feeding the aqueous liquid solution of hydrogen peroxide to the means of subparagraph (b) of the foregoing apparatus;

(b) feeding the air to the means of subparagraph (c) of that apparatus; and (c) operating that apparatus to produce the flow of a gas-phase mixture of air and vaporized hydrogen peroxide of substantially constant hydrogen peroxide concentration as a function of time.

In another aspect, the invention concerns an apparatus that can produce at high vaporization efficiency from a gas or vapor comprising a first substance and a vaporizable liquid comprising a second substance a substantially continuous flow of a low-temperature unsaturated gas-phase mixture of the first substance and vaporized second substance of substantially constant second substance concentration as a function of time, said apparatus comprising:

(a) a vaporization plenum having an inner surface;

(b) means for breaking the liquid into fine particles and for flowing the fine particles in the vaporization plenum, the bulk flow of the fine particles flowing in the vaporization plenum being in a first direction;

(c) means for flowing the first substance in the vaporization plenum and for flowing at least some of the first substance between the inner surface of the vaporization plenum and substantially all of the fine particles to create a curtain of first substance between the inner surface of the vaporization plenum and substantially all of the fine particles, the bulk flow of the first substance in the vaporization plenum flowing in substantially the same direction as the first direction; and (d) means for causing substantially all of the fine particles to vaporize in the flow of the first substance to produce a flow of a gas-phase mixture of the first substance and vaporized second substance of substantially constant second substance concentration as a function of time.

In another aspect, the invention concerns a method for producing at high vaporization efficiency from a gas or vapor comprising a first substance and a vaporizable liquid comprising a second substance a flow of a low-temperature unsaturated gas-phase mixture of the first substance and vaporized second substance of substantially constant second substance concentration as a function of time, said method comprising:

(a) feeding the liquid comprising the second substance to the means of subparagraph (b) of the immediately foregoing apparatus;

(b) feeding the gas or vapor comprising the first substance to the means of subparagraph (c) of that apparatus; and (c) operating that apparatus to produce the flow of a gas-phase mixture of the first substance and vaporized second substance of substantially constant second substance concentration as a function of time.

In preferred embodiments, the vaporizing (e.g., carrier) gas or vapor (e.g., air) flows between the inner surface of the vaporization plenum and substantially all of the fine particles of the second substance (e.g., a liquid solution of hydrogen peroxide) to create the curtain of first substance; the vaporizing gas or vapor flows into the vaporization plenum through openings (e.g., holes, arcuate slots) that are symmetrically arranged around an imaginary line; the particles of vaporizable second substance are introduced into the flow of the vaporizing gas or vapor at a point along the imaginary line; the apparatus is oriented so that the bulk flow in the vaporization plenum is up and substantially vertical; an ultrasonic device is used to produce the fine particles from the bulk liquid; the inner surface of the vaporization plenum is substantially parallel to the imaginary line; and the flow of the gas-phase mixture of the first substance and vaporized second substance is substantially continuous.

This invention provides apparatus and method for producing hydrogen peroxide vapor-air mixtures that have a substantially constant concentration of hydrogen peroxide as a function of time and that need not be saturated with the hydrogen peroxide. Moreover, the apparatus and method of this invention can produce such mixtures at low air flow rates and at low temperature. More generally, the apparatus and method can be used with other vaporizing (carrier) gases or vapors instead of air and with vaporizable liquids other than hydrogen peroxide solutions. This invention has still other features and benefits that will be apparent to one skilled in the art.

BRIEF DESCRIPTION OF THE DRAWINGS

To facilitate further description of the invention, the following drawings are provided in which:

FIG. 1 is a side sectional view of a first apparatus according to this invention for producing hydrogen peroxide vapor-air mixtures;

FIG. 2 is a side sectional view of a second apparatus according to this invention for producing hydrogen peroxide vapor-air mixtures;

FIG. 3 is a view of the vaporization plenum of a device of FIG. 1 or FIG. 2 looking down in FIG. 1 or 2 with conduit 56 and nipple 52 removed and showing a preferred air distributor and ultrasonic nozzle in the middle; and FIG. 4 is a view similar to that of FIG. 3 but with an alternative air distributor.

These drawings are provided for illustrative purposes only and should not be used to unduly limit the scope of the invention.

DETAILED DESCRIPTION OF THE INVENTION

The apparatus and method of the present invention can be used for producing a gas-phase flow of a carrier vapor or gas combined with and containing the vapor resulting from vaporizing a liquid. The bulk liquid fed to the apparatus is converted by the apparatus into particulates and those particulates are entrained in the carrier. The carrier is in the gas phase and is a gas or is a liquid that has already been vaporized. The carrier entrains the particles of liquid of the vaporizable liquid and acts to vaporize those particles. Vaporization desirably occurs rapidly for a number of reasons, including that the surface area of the particulates is large compared to their volume (or mass) and that at the temperature of the carrier and particulates, the vapor pressure of the vaporizable liquid is sufficiently high. If the carrier is itself a vapor, the temperature should be high enough so that the carrier vapor does not condense.

It is a feature of this invention that it can provide a product (i.e., effluent from the apparatus) that contains substantially no liquid, i.e., is substantially in the gas phase. In other words, it is a feature of this invention that a sufficient proportion of the fine particles are vaporized in the apparatus so that the effluent from the apparatus contains substantially no liquid, i.e., is substantially in the gas phase. Thus, the effluent will contain no more than 10% w/w liquid-phase material, desirably no more than 8% w/w, more desirably no more than 6% w/w, most desirably no more than 4% w/w, preferably no more than 2% w/w, more preferably no more than 1% w/w, and most preferably no more than 0.5% w/w liquid-phase material.

It is a feature of this invention that the temperature of the gas-phase flow produced by the apparatus and method of the invention can be (but need not be) relatively low. In other words, the temperature need not be anywhere as high as the boiling point of the vaporizable liquid. By "low-temperature," a "relatively low" temperature, and the like in connection with the gas-phase flow is meant a temperature below the boiling point, usually at least 20° C., desirably at least 30° C., more desirably at least 40° C., most desirably at least 50° C., preferably at least 60° C., more preferably at least 70° C., most preferably at least 80° C., and possibly even at least 90° C. lower than the boiling point of the vaporizable liquid.

The normal (atmospheric) boiling point of hydrogen peroxide is approximately 151° C. Thus, for hydrogen peroxide, the apparatus and method of the invention when operated at atmospheric pressure can produce a gas-phase flow containing vaporized hydrogen peroxide at a temperature less than the normal boiling point and desirably much lower. At atmospheric pressure, the boiling point of pure water is 100° C. The apparatus and method of the invention when operated at atmospheric pressure can produce a gas-phase flow containing vaporized water at a temperature less than the normal boiling point and desirably much lower. When using a 30% w/w aqueous solution of hydrogen peroxide as the vaporizable liquid (the normal boiling point of which is approximately 105° C.), the apparatus and method of the invention when operated at approximately atmospheric pressure can produce a gas-phase flow of air as the carrier containing the completely vaporized aqueous hydrogen peroxide solution at temperatures that are as low as 0° C. to 80° C.

As will be understood by one skilled in the art, the heat needed to vaporize the vaporizable liquid (latent heat of vaporization) will be supplied by (transferred from) the carrier gas and will also be supplied by the vaporizable liquid itself. Thus, the carrier gas and the vaporizable liquid may enter the vaporization plenum at a temperature somewhat higher than the temperature of the final gas-phase product leaving the vaporization plenum. The vaporization of the vaporizable liquid will reduce the sensible temperature of the gas-phase mixture leaving the vaporization plenum if no other heat is added to the system. However, additional heat can be supplied to the system through, for example, the wall of the vaporization plenum. That additional heat may be the same as or more or less than the amount of heat required to vaporize the vaporizable liquid, thereby allowing further control of the temperature of the final gas-phase mixture.

It is a feature of this invention that it allows such fine control that the vaporized vaporizable liquid in the total (effluent product) gas-phase flow can be present in any amount, namely, complete saturation or any level of unsaturation (i.e., from more than 99% of saturation to less than 1% of saturation). In this context, the term "unsaturated," "unsaturation," and the like refer to the vaporized vaporizable liquid not being present in the gas-phase product of the apparatus of this invention in the amount that would constitute full saturation under the specified conditions.

It is another feature of this invention that its method and apparatus can (but do not have to) produce a gas-phase flow containing a substantially constant concentration of the vaporized vaporizable liquid (also referred to as the "second substance") over the time period of interest. By "substantially constant hydrogen peroxide concentration as a function of time," "substantially constant second substance concentration as a function of time," and the like is meant that the concentration of the hydrogen peroxide or other second substance (vaporizable liquid) in the gas-phase flow remains substantially constant over the time period of interest. In this context, "substantially constant" means that over the time period of interest, no concentration within that time period varies from the mean time-averaged concentration over that period by more than plus or minus 15%, desirably by no more than plus or minus 10%, more desirably by no more than plus or minus 8%, most desirably by no more than plus or minus 6%, preferably by no more than plus or minus 4%, more preferably by no more than plus or minus 2%, and most preferably by no more than plus or minus 1%. In other words, none of the instantaneously measured concentrations of the hydrogen peroxide or other second substance deviates from the average by more than plus or minus 15% of the average value, desirably by no more than plus or minus 10% of the average value, more desirably by no more than plus or minus 8%, etc.

Separate and apart from the "substantially constant" concentration of the hydrogen peroxide or other vaporized vaporizable liquid in the gas-phase flow, it is also a feature of this invention that the gas-phase flow (i.e., the entire flow out of the apparatus) can be (but does not need to be) "substantially continuous," by which is meant that the flow satisfies at least one of the following criteria: (a) over the time period of interest, the minimum flow out of the apparatus is at least 50% (desirably at least 60%, more desirably at least 70%, most desirably at least 75%, preferably at least 80%, more preferably at least 85%, and most preferably at least 90%) of the maximum flow out of the apparatus, or (b) over the time period of interest, each of the minimum and maximum flows out of the apparatus differ from the time-average flow out of the apparatus by no more than 30% (desirably by no more than 25%, more desirably by no more than 20%, most desirably by no more than 15%, preferably by no more than 12.5%, more preferably by no more than 10%, and most preferably by no more than 7.5%) of the time-average flow out of the apparatus, or (c) over the time period of interest, the time-average flow for each successive minute long period is at least 60% (desirably at least 70%, more desirably at least 75%, most desirably at least 80%, preferably at least 85%, more preferably at least 90%, and most preferably at least 95%) of the time-average flow out of the apparatus.

The fine particles of vaporizable liquid that are introduced into the flow of the carrier gas or vapor (i.e., the first substance) are desirably as small as possible so that the surface-to-volume (or mass) ratio is as large as is needed to allow the advantages of this invention to be achieved. Particle sizes in the micron range will generally be used. Thus, the average particle size can range from 10 to 100 microns (desirably 10 to 50 microns), although smaller and larger particles may be used in certain cases. For example, if the flow of carrier gas or vapor is high compared to the flow of particles of vaporizable liquid, the temperatures are high enough, the vapor pressure of the vaporizable liquid is relatively high, the vaporization plenum is long enough, and the final concentration of vaporized vaporizable liquid in the gas-phase flow to be produced by the apparatus is not too close to saturation, the particles may be relatively larger than they would otherwise need to be. For 30% w/w aqueous hydrogen peroxide, an average particle size of 18 microns has been found to be satisfactory for the device described below. Desirably, the distribution of particle sizes is not too broad. In other words, preferably, 80% or more of the particles are within plus or minus 70% of the average particle size.

Breaking the vaporizable liquid into fine particles can be accomplished in any way that provides particles that are small enough and that flow inside the vaporization plenum in the desired direction. Devices such as atomizers or ultrasonic devices may be used. For a 30% w/w aqueous solution of hydrogen peroxide, a Sono-Tek brand ultrasonic device (Nozzle Model No. 12385, Generator Model No. 06-05112) has been found to be satisfactory as part of the apparatus described below.

The vaporization plenum can have any size or shape that allow the advantages of this invention to be achieved, although a cylindrical shape is preferred. The material of construction for the vaporization plenum and the rest of the apparatus can be anything that is sufficiently inert with respect to the substances that are present, e.g., flowing in the vaporization plenum. Thus, for a final gas-phase flow of air, water, and hydrogen peroxide (the hydrogen peroxide and most, if not all, of the water coming from the vaporizable liquid when it is an aqueous solution of hydrogen peroxide), the vaporization plenum can be made of aluminum (e.g., 6061 non-anodized), stainless steel (e.g., type 316 stainless steel), or any other suitable material.

An important feature of this invention is that in the vaporization plenum, the first substance (e.g., air) and the fine particles of the second substance (e.g., aqueous solution of hydrogen peroxide) are introduced in such a way that the particles are kept from touching the inner surface of the vaporization plenum. That is done because liquid particles that contact the inner surface of the vaporization plenum are less likely to be vaporized and/or are less likely to be vaporized completely. That results in the effluent gas-phase flow not having a substantially constant concentration of the vaporizable substance as a function of time. In other words, because it is important that the concentration of the vaporizable substance be substantially constant as a function of time, the particles of that substance introduced into the vaporization plenum must vaporize completely but if those particles contact the inner surface of the vaporization plenum, it reduces the chances of such complete vaporization.

If the vaporization plenum is cylindrical and the bulk flow is from one circular end (i.e., the entrance) of the cylinder towards the other end (i.e., the exit end), the particles of vaporizable liquid may be introduced at any point along the longitudinal center line of the vaporization plenum between the two ends (provided substantially complete vaporization of the vaporizable liquid occurs), with the bulk flow of the particles flowing towards the exit end of the vaporization plenum. Regardless of the shape of the vaporization plenum, the first substance (the carrier) may be introduced in any manner and in any orientation that places at least some (i.e., at least a sufficient amount) of the first substance between the inner surface of the vaporization plenum and substantially all of the fine particles to provide a curtain of the first substance between the inner surface of the vaporization plenum and substantially all of the fine particles. There may be more than one point of introduction into the vaporization plenum of each of the first and second substances, and those points may or may not be symmetrically arranged (e.g., may or may not be symmetrically arranged around the longitudinal centerline of the vaporization plenum).

Providing the curtain of carrier is an important feature of this invention because the presence of that curtain greatly diminishes the number of collisions of the fine particles of the vaporizable substance with the inner surface of the vaporization plenum by keeping the particles away from the inner surface. Therefore, any method of introducing the first substance and fine particles of second substance into the vaporization plenum can be used as long as a curtain of the first (carrier) substance is provided to shield the inner surface of the vaporization plenum from substantially all of the fine particles. In this context, the term "substantially all of the fine particles" and like terms mean that no more than 10%, desirably no more than 8%, more desirably no more than 6%, most desirably no more than 4%, preferably no more than 2%, more preferably no more than 1%, and most preferably no more than 0.5% of the fine particles contact the inner surface of the vaporization plenum. Ideally no more than 0.1% of the fine particles contact the inner surface of the vaporization plenum.

The curtain need not be of uniform thickness. Thus, for example, with a cylindrical vaporization plenum, it is not necessary that the first substance (carrier), e.g., air, be introduced through an annular ring of constant width (which would tend to make the curtain of the carrier of uniform thickness. The carrier can have any flow pattern that provides the benefits of this invention. For example, the curtain may have a spiral or corkscrew flow pattern, which could be achieved by introducing the carrier into the vaporization plenum through passageways at an acute angle to the inner surface of the vaporization plenum.

The second substance (the vaporizable liquid) may be introduced into the vaporization plenum in any manner and in any orientation. The fine particles of the second substance (vaporizable liquid) need not be introduced at only one point into the vaporization plenum. For example, the carrier and particles of vaporizable liquid may each be introduced through a number of different openings into the vaporization plenum and those openings may be distributed or interspersed among each other. The only requirement is that the curtain of carrier (first substance) be created.

As will be understood by one skilled in the art, in addition to the temperature of the first and second substances and the size of the fine particles, another factor that helps determine whether a sufficient amount of the fine particles are vaporized so that the effluent from the apparatus contains substantially no liquid (i.e., is substantially in the gas phase) is the residence time of the fine particles in the apparatus. That in turn depends on the length of the device and the linear velocity of the particle flow.

The velocity of the fine particles when they are first injected into the vaporization plenum is desirably not greater than the velocity of the carrier. In any case, for several reasons, including the relative mass flows of the carrier and fine particles, the fine particles rapidly assume substantially the same velocity and direction as the carrier and therefore are carried towards the exit of the apparatus by the carrier (i.e., the first substance, which is a gas or is itself a vapor) at substantially the same linear velocity as the linear velocity of the first substance (carrier). Depending on the size, shape, and density of the fine particles, the density of the carrier, etc., the linear velocity of the carrier may vary from 0.1 centimeters/second to more than 50 centimeters/second but generally will be in the range of 0.1 to 25, desirably 0.1 to 10, and preferably from 0.1 to 5 centimeters/second.

The direction of the bulk flow of a fluid (carrier, fine particles of vaporizable liquid, vaporized vaporizable liquid) in the apparatus is the major or principal direction of the overall flow and ignores the intermixing, lateral movement, etc. of the individual volumetric subdivisions (i.e., packets) of the fluid. For the entire apparatus, the direction of bulk flow is from the introduction of that fluid to the exit of the device; however, at any point along the fluid path inside the apparatus, the direction of bulk flow may be at any orientation with respect to the direction of the overall flow. That is because the fluid path inside the apparatus need not be straight from entrance to exit and can have any path, bent, crooked, winding, serpentine, spiral or corkscrew, or otherwise. However, as will be understood by one skilled in the art, a straight path, particularly in the vaporization plenum, is preferred.

The apparatus can be oriented so that the direction of bulk flow for the entire apparatus is in any direction and so that the direction of bulk flow of the fluid inside the vaporization plenum is in any direction; however, preferably the direction of bulk flow of all fluids inside the vaporization plenum has an upward vertical component and preferably is substantially upwardly vertical. By the term "substantially upwardly vertical," "up and substantially vertical," and the like is meant that the direction of bulk flow of the fluid inside the vaporization plenum is up and does not deviate from the vertical by more than 25°, desirably by no more than 20°, more desirably by no more than 15°, most desirably by no more than 10°, preferably by no more than 5°, more preferably by no more than 2°, and most preferably by no more than 1°. A substantially upwardly vertical flow of the fluid inside the vaporization plenum helps increase the chances that the fine particles of vaporizable liquid will be substantially all vaporized in the vaporization plenum. If the direction of bulk flow of the fluid inside the vaporization plenum is other than substantially upwardly vertical, it increases the chances that the fine particles of vaporizable liquid will contact the inner surface of the vaporization plenum and not be completely and rapidly vaporized.

For a droplet about 20 microns in diameter having a specific gravity of about 1.1 (i.e., a density of about 1.1 grams/cubic centimeter), with air as the carrier, operating around atmospheric pressure and at a temperature of about 50° C., and in a device in which the bulk flow of the fluid inside the vaporization plenum is vertical (i.e., directly against the force of gravity), the calculated minimum linear velocity of the air is approximately 2.7 centimeters per second (based on certain assumptions made concerning various factors, e.g., drag coefficient) so that the droplet is buoyed by the air flow and does not fall down. That velocity can be provided by adjusting the volumetric (or mass) flow of the air into the device and/or by choosing an appropriate vaporization plenum cross-sectional area. As will be understood by one skilled in the art, the linear flow of carrier needed to provide sufficient lift to a particle depends on a number of factors, including the particle size and shape, the density of the particle, and the density of the carrier. As will be understood by one skilled in the art, if the theoretical minimum linear velocity of the air should be approximately 2.7 centimeters per second, the minimum linear velocity of air leaving the openings that feed the air into the vaporization plenum should be substantially higher (principally because the cross-sectional area of the openings is much smaller than the cross-sectional area of the vaporization plenum).

With this background, we turn to FIG. 1, which is a cross-sectional view of one embodiment of the invention. Apparatus 10 comprises cylindrical vaporization plenum 12 having inner surface 14. Vaporization plenum is bounded at its ends by surface 38 of cylindrical end block 32 and exit 72. Cylindrical end block 32 is held in place by screws 46.

Screws 48 hold inner collar or ring 50 in place near exit 72. Inner ring 50 is threaded on its inner surface. Threaded portion 54 of nipple 52 screws into inner ring 50. Conduit 56 is press-fit onto nipple 52 and is also held in place by a circumferential compression band (not shown). Conduit 56 provides a passageway for the gas-phase effluent to leave the apparatus.

Figure 3:
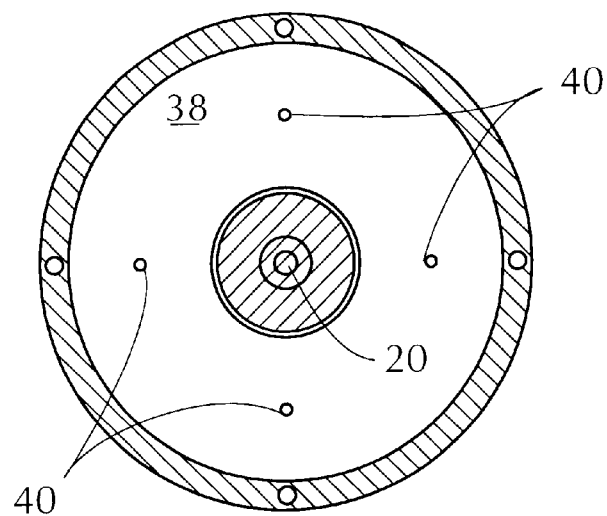
Figure 4:
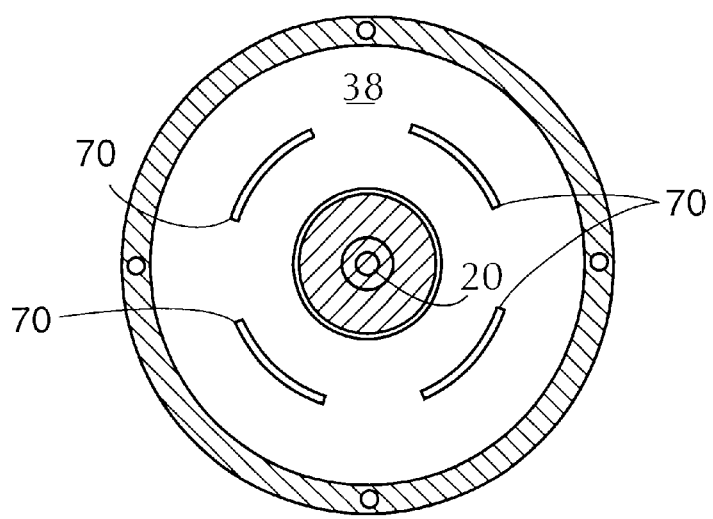

Warm dry air is introduced into vaporization plenum 12 through tube 26, which is connected to nozzle 28. The feed air flows through nozzle 28 into toroidal plenum 36, fills the toroidal plenum, and flows into vaporization plenum 12 through four openings 40 (only two of which are shown in FIG. 1; all four openings 40 are shown in FIG. 3). Air flow lines 42, whose direction of bulk flow is indicated by parallel arrows 44, illustrate the flow of air into vaporization plenum 12. As will be understood by one skilled in the art, the streamlines of air jetting out of openings 40 fan out.

Ultrasonic unit 18 is powered through an electric cord (not shown). Screw 34 holds plate 30 tightly against the outer surface of cylindrical end block 32, thereby holding ultrasonic unit 18 in place. Hydrogen peroxide solution (30% w/w aqueous solution) flows through inlet (feed) tube 17 into the ultrasonic unit, in which the flow of liquid is broken into fine particles approximately 18 microns in diameter.

The fine particles of the vaporizable liquid (the 30% w/w aqueous solution) are flowed into vaporization plenum 12 through nozzle 20. Flow lines 22 indicate the flow of fine particles out of nozzle 20, and arrow 24 signifies the direction of bulk flow of those particles. That direction of bulk flow lies on imaginary centerline 16 of vaporization plenum 12, which line intersects surface 38 at a point (not shown). (As will be understood by one skilled in the art, centerline 16 continues without limit above the vaporization plenum and also runs through the longitudinal center of nozzle 20, through the rest of ultrasonic unit 18, and continues without limit below the apparatus.) The direction of bulk flow of the fine particles (arrow 24) and the direction of bulk flow of the air (arrows 44) are parallel to each other, i.e., lie in the same direction, and both are vertical. The direction of bulk flow of the air (arrows 44) is also parallel to centerline 16 of vaporization plenum 12. Finally, centerline 16, the direction of bulk flow of the fine particles (arrow 24), and the direction of bulk flow of the air (arrows 44) are also each parallel to the inner surface of cylindrical vaporization plenum 12. When referring to these lines and/or surfaces, by "substantially parallel" is meant that the lines and/or surfaces do not deviate from being parallel by more than 40°, desirably by no more than 20°, more desirably by no more than 15°, most desirably by no more than 10°, preferably by no more than 5°, more preferably by no more than 2°, and most preferably by no more than 1°.

As shown in FIGS. 1 and 3, openings 40 are symmetrically arranged around centerline 16, which line passes through the central opening of nozzle 20 from which the fine particles of liquid flow into the air in the vaporization plenum. Thus, the flow of fine particles is introduced into the flow of air along a line about which openings 40 are symmetrically located.

In this device, all of the air flows into the vaporization plenum between inner surface 14 of the vaporization plenum and the point at which the fine particles are fed (i.e., the tip of nozzle 20), and that air creates a curtain of air between substantially all of the fine particles and the inner surface of the vaporization plenum.

A device in accordance with FIGS. 1 and 3 was built and tested. A cylindrical 6061 non-anodized aluminum pipe with a wall thickness of about 0.25 inches (about 6.4 millimeters) was used for the vaporization plenum. Stainless steel (e.g., type 316) could also have been used. Whatever the material of construction, it desirably is machinable as well as being sufficiently inert to the fluids to be processed in it. The inner diameter of the pipe was approximately 4.5 inches (approximately 114 millimeters) and the length of the vaporization plenum (from inner surface 38 of cylindrical end block 32) to the beginning of nipple 52 was approximately 7 inches (178 millimeters) long. Cylindrical end block 32 was approximately 1.45 inches thick (37 millimeters). Toroidal plenum 36 had an inner diameter of approximately 2.25 inches (57 millimeters), was approximately 0.5 inches (12.7 millimeters) high, and its upper surface lay approximately 0.2 inches (5 millimeters) below inner surface 38. The ultrasonic unit was a Sono-Tek brand device (Nozzle Model No. 12385, Generator Model No. 06-05112). An electrical heating tape was wrapped around the outside of vaporization plenum 12 and sufficient heat was supplied to keep the temperature of the vaporization plenum wall above 30° C. (ambient temperature was approximately 22° C.). Conduit 56 was left uninsulated to allow heat to leave the system so that the temperature of the gas-phase flow of air and vaporized hydrogen peroxide aqueous solution would fall.

Warm dry (−40° C. dew point) air at 50° C. was introduced through tube 26 at the rate of 30 liters/minute (500 cubic centimeters/second). Flow was controlled using a Norgren proportional pressure control valve, Model No. VP5002PK4111100, and a Norgren in-line flow control valve, Model No. T1000A2800. Temperature was controlled using a Hot Watt air process heater, Model No. AH37-A-MF, and a Watlow temperature controller, Model Series 965. Aqueous hydrogen peroxide solution (30% w/w) at a temperature of 22° C. was fed to the ultrasonic unit at a rate of 180 microliters/minute). Flow was controlled using a Digichrom syringe pump, Model No. 2Q. The particles produced by the ultrasonic unit were approximately 18 microns in diameter.

At first, each of the four opening 40 was approximately 0.5 inches (12.7 millimeters) in diameter; however, the concentration of hydrogen peroxide in the resulting effluent gas-phase mixture was not as high as the calculated theoretical concentration. When the device was opened for visual inspection to determine the cause of the discrepancy, it was discovered that some of the fine particles of hydrogen peroxide solution had not been vaporized and had instead contacted the inner surface of the vaporization plenum and pooled and collected. Because the pooling occurred on the side of the vaporization plenum distant from air feed nozzle 28, it was suspected that that the linear velocity of air through the one or two openings 40 distant from air feed nozzle 28 was not high enough (as compared to the linear velocity of air flowing out of the openings closer to air feed nozzle 28) to keep the fine particles flowing out of ultrasonic nozzle 20 from contacting the inner surface on that distant side of the vaporization plenum. When smaller openings 40 approximately one-sixteenth of an inch (1.6 millimeters) in diameter were used (to try to equalize the flows out of the four openings 40), the pooling problem substantially disappeared and the hydrogen peroxide in the gas-phase effluent was therefore closer to the calculated theoretical value of about 2.0 milligrams of hydrogen peroxide per liter.

With the air and hydrogen peroxide solution flow rates and temperatures noted above, the concentration of hydrogen peroxide in the gas-phase effluent from the apparatus when equipped with the one-sixteenth inch holes was 1.8 milligrams of hydrogen peroxide per liter (about 90% of the calculated theoretical value of about 2.0 milligrams/liter). The temperature of the effluent was 30° C., at which temperature the saturation limit for air is approximately 3 milligrams per liter. Therefore, the apparatus was producing a gas-phase effluent that was approximately 60% saturated with respect to the hydrogen peroxide (1.8 divided by 3).

As a result, it is believed that the flow of carrier through the openings providing the curtain of carrier between the fine particles of the vaporizable liquid and the inner wall of the vaporization plenum should be "substantially equal." In this context, the term "substantially equal" and the like mean that the flow through any one of those openings should not deviate from the average value of the flow through all of those openings by more than 35% of the average value, desirably by no more than 30%, more desirably by no more than 25%, most desirably by no more than 20%, preferably by no more than 15%, more preferably by no more than 10%, and most preferably by no more than 5%.

Because of the inherent difficulty in producing equal air (carrier) flows through openings 40 when the point of introduction of the air into cylindrical end block 32 is closer to some of the openings than to others, a new design for the block was developed and is shown in FIG. 2. Air feed nozzle 28 is now centrally located and an internal X-shaped header comprising two elongate horizontal bores or passageways 58 at 90° to each other is used. The air is introduced through nozzle 28 at the center of the X, i.e., in the longitudinal (axial) center of cylindrical end block 32, where the two bores 58 intersect (in FIG. 2, only one of the bores 58 is shown). A plug 60 at the end of each bore 58 keeps the air from flowing out of cylindrical end block 32.

Four vertical bores or passageways 62 (only two of which are shown) are fluidly connected to the four legs of the X-shaped header formed by horizontal bores 58. Each bore 62 is capped by a plug 64 (only two of which are shown). A small diameter opening 40 of approximately one-sixteenth inch (1.6 millimeters) through each plug 64 allows air to flow into vaporization plenum 12. O-ring 66 between ultrasonic unit 18 and the larger cavity provided for it in cylindrical end block 32 and O-ring 68 between cylindrical end block 32 and the end of the pipe forming vaporization plenum 12 prevent fluid leakage, which was thought to be a problem with the device of FIG. 1.

The device of FIG. 2 is an improvement over the device of FIG. 1: it is believed to provide a more equal air flow through the four openings 40 than did the device of FIG. 1 even when the FIG. 1 device was equipped with the smaller openings. The device of FIG. 2 was operated with the same inlet flows and other conditions as the device of FIG. 1, and the resulting hydrogen peroxide concentration in the effluent from the device was 2 milligrams/liter, as compared to 1.8 milligrams/liter for the device of FIG. 1 with the smaller (one-sixteenth inch) holes. Thus, the vaporization efficiency of the device of FIG. 2 was almost 100% (as compared to the 90% vaporization efficiency of the FIG. 1 device with the smaller (one-sixteenth inch) holes. The effluent temperature was again 30° C., at which temperature the saturation limit for air is approximately 3 milligrams of hydrogen peroxide per liter. Thus, the gas-phase effluent was approximately 67% saturated with respect to hydrogen peroxide (2 divided by 3) but the vaporization efficiency was almost 100%. This demonstrates that the apparatus of this invention can produce gas-phase effluents at virtually 100% vaporization efficiency but that are substantially less than saturated with respect to the vaporizable liquid.

It is a feature of this invention that the vaporization efficiency of its embodiments (i.e., the percentage of vaporized vaporizable liquid in the gas-phase effluents from those embodiments) can be (but does not necessarily have to be) a high percentage of the calculated theoretical value (calculated assuming that all of the vaporizable liquid fed to an embodiment is vaporized and is well-mixed with the carrier gas or vapor). As used herein, the terms "high vaporization efficiency," "highly efficient with respect to vaporization," and the like refer to the embodiments being able to produce effluents having such high percentages. Generally, the "high vaporization efficiency" of the embodiments of this invention will be at least 80%, desirably at least 85%, more desirably at least 90%, most desirably at least 95%, preferably at least 97%, more preferably at least 99%, most preferably at least 99.5%, and in some cases 100%.

FIG. 4 shows a conceptual alternative design for the openings through which the carrier can be introduced (not yet built or tested). Arcuate slots 70 are symmetrically arranged around nozzle 20 of the ultrasonic unit and, as shown in FIGS. 1 and 2, the longitudinal centerline of nozzle 20 and arrow 24 lie along centerline 16 of vaporization plenum 12.

For a given carrier flow or range of carrier flows, one skilled in the art will know how to vary the shape and dimensions of the one or more slots (or other openings) to provide the necessary curtain of carrier to keep substantially all of the fine particles of the vaporizable liquid from the inner surface of the vaporization plenum.

The size of the openings through which the carrier is introduced will generally vary from less than a millimeter in equivalent diameter to 50 millimeters or more, depending on the flowrate of the carrier (by "equivalent diameter" is mean the diameter of a circle that would have the same area as the opening in question). For laboratory size units, the equivalent diameter will usually be from 0.1 millimeters to 25 millimeters, desirably from 0.1 to 20 millimeters, more desirably from 0.1 to 15 millimeters, preferably from 0.1 to 10 millimeters, more preferably from 0.1 to 5 millimeters, and most preferably from 0.1 to 2.5 millimeters. At least some of the carrier may be introduced into the vaporization plenum through members containing micropores, such as are present in sintered objects (e.g., sintered metal discs), provided the required curtain of carrier is formed.

The feed flowrates in the embodiments discussed above were 30 liters/minute of dry warm air and 180 microliters/minute of 30% w/w aqueous hydrogen peroxide solution. The range of feed flows can be from less than 1 liter per minute to hundreds or even more liters/minute of carrier and from just a few microliters per minute of vaporizable liquid to many liters per minute. Of course, the apparatus can be scaled up to provide even larger flows and/or be used at pressures other than atmospheric and/or be used at high temperatures; however, the apparatus of this invention is particularly useful for producing, at high vaporization efficiency, low volume substantially continuous gas-phase flows at atmospheric pressure and at low temperature (e.g., an effluent temperature of 0–80° C. when hydrogen peroxide is the second substance derived from a 30% w/w aqueous solution of hydrogen peroxide) of substantially constant second substance (e.g., hydrogen peroxide) concentration even at second substance concentration levels below (even well below) saturation. The precisely controllable, continuously adjustable gas-phase flows produced by this invention are of particular use in, for example, testing and analytical devices. Thus, the effluent flow rates will typically be from 0.1 liters per minute to 500 liters per minute, desirably from 0.5 to 250 liters/minute, more desirably from 0.5 to 200 liters/minute, preferably from 0.5 to 150 liters/minute, more preferably from 0.5 to 100 liters/minute, and most preferably from 0.5 to 50 liters/minute.

Variations and modifications will be apparent to those skilled in the art and the following claims are intended to cover all variations and modifications falling within the true spirit and scope of the invention.

We claim:

1. An apparatus that can produce at high vaporization efficiency from air and an aqueous liquid solution of hydrogen peroxide a substantially continuous flow of a low-temperature unsaturated gas-phase mixture of air and vaporized hydrogen peroxide of substantially constant hydrogen peroxide concentration as a function of time, said apparatus comprising:
   (a) a vaporization plenum having an inner surface;
   (b) means for breaking the aqueous liquid solution of hydrogen peroxide into fine particles and for flowing the fine particles in the vaporization plenum, the bulk flow of the fine particles flowing in the vaporization plenum being in a first direction;
   (c) means for flowing the air in the vaporization plenum and for flowing at least some of the air between the inner surface of the vaporization plenum and substantially all of the fine particles to create a curtain of air between the inner surface of the vaporization plenum and substantially all of the fine particles, the bulk flow of the air in the vaporization plenum flowing in substantially the same direction as the first direction; and
   (d) means for causing substantially all of the fine particles to vaporize in the flow of the air to produce a flow of a gas-phase mixture of air and vaporized hydrogen peroxide of substantially constant hydrogen peroxide concentration as a function of time.

2. The apparatus of claim 1 wherein the means of subparagraph (c) comprises means for flowing substantially all of the air fed to the vaporization plenum between the inner surface of the vaporization plenum and substantially all of the fine particles to create the curtain of air.

3. The apparatus of claim 1 wherein the means of subparagraph (c) comprises a surface having a plurality of openings through which the air is fed that are arranged symmetrically around a line passing through the surface.

4. The apparatus of claim 3 wherein the means of subparagraph (b) introduces at least some of the flow of fine particles into the flow of air at a location along the line that passes through the surface.

5. The apparatus of claim 3 wherein the plurality of openings are equidistant from the line passing through the surface.

6. The apparatus of claim 3 wherein at least some of the openings are holes.

7. The apparatus of claim 3 wherein at least some of the openings are slots.

8. The apparatus of claim 7 wherein the slots are arcuate slots.

9. The apparatus of claim 1 wherein the apparatus is oriented so that the first direction is up.

10. The apparatus of claim 9 wherein the apparatus is oriented so that the first direction is substantially vertical.

11. The apparatus of claim 1 wherein the means of subparagraph (b) comprises an ultrasonic device.

12. The apparatus of claim 1 further comprising an outlet for the gas-phase mixture of air and vaporized hydrogen peroxide wherein the first direction is in the direction of the outlet.

13. The apparatus of claim 1 wherein the inner surface of the vaporization plenum is substantially parallel to a line lying in the first direction.

14. A method for producing at high vaporization efficiency from air and an aqueous liquid solution of hydrogen peroxide a flow of a gas-phase mixture of air and vaporized hydrogen peroxide of substantially constant hydrogen peroxide concentration as a function of time, said method comprising:
   (a) feeding the aqueous liquid solution of hydrogen peroxide to the means of subparagraph (b) of claim 1;
   (b) feeding the air to the means of subparagraph (c) of claim 1; and
   (c) operating the apparatus of claim 1 to produce the flow of a gas-phase mixture of air and vaporized hydrogen peroxide of substantially constant hydrogen peroxide concentration as a function of time.

15. The method of claim 14 in which the temperature and amount of aqueous liquid solution of hydrogen peroxide fed in step (a), the temperature and amount of air fed in step (b), and the operation of the apparatus are such that the gas-phase mixture of air and vaporized hydrogen peroxide produced is low-temperature or unsaturated or both low-temperature and unsaturated.

16. The method of claim 14 in which the flow of the gas-phase mixture of air and vaporized hydrogen peroxide is substantially continuous.

17. An apparatus that can produce at high vaporization efficiency from a gas or vapor comprising a first substance and a vaporizable liquid comprising a second substance a substantially continuous flow of a low-temperature unsaturated gas-phase mixture of the first substance and vaporized second substance of substantially constant second substance concentration as a function of time, said apparatus comprising:

(a) a vaporization plenum having an inner surface;

(b) means for breaking the liquid into fine particles and for flowing the fine particles in the vaporization plenum, the bulk flow of the fine particles flowing in the vaporization plenum being in a first direction;

(c) means for flowing the first substance in the vaporization plenum and for flowing at least some of the first substance between the inner surface of the vaporization plenum and substantially all of the fine particles to create a curtain of first substance between the inner surface of the vaporization plenum and substantially all of the fine particles, the bulk flow of the first substance in the vaporization plenum flowing in substantially the same direction as the first direction; and (d) means for causing substantially all of the fine particles to vaporize in the flow of the first substance to produce a flow of a gas-phase mixture of the first substance and vaporized second substance of substantially constant second substance concentration as a function of time.

18. The apparatus of claim 17 wherein the means of subparagraph (c) comprises means for flowing substantially all of the first substance fed to the vaporization plenum between the inner surface of the vaporization plenum and substantially all of the fine particles to create the curtain of first substance.

19. The apparatus of claim 17 wherein the means of subparagraph (c) comprises a surface having a plurality of openings through which the first substance is fed that are arranged symmetrically around a line passing through the surface.

20. The apparatus of claim 19 wherein the means of subparagraph (b) introduces at least some of the flow of fine particles into the flow of first substance at a location along the line that passes through the surface.

21. The apparatus of claim 19 wherein the plurality of openings are equidistant from the line passing through the surface.

22. The apparatus of claim 19 wherein at least some of the openings are holes.

23. The apparatus of claim 19 wherein at least some of the openings are slots.

24. The apparatus of claim 23 wherein the slots are arcuate slots.

25. The apparatus of claim 17 wherein the apparatus is oriented so that the first direction is up.

26. The apparatus of claim 25 wherein the apparatus is oriented so that the first direction is substantially vertical.

27. The apparatus of claim 17 wherein the means of subparagraph (b) comprises an ultrasonic device.

28. The apparatus of claim 17 further comprising an outlet for the gas-phase mixture of first substance and vaporized second substance wherein the first direction is in the direction of the outlet.

29. The apparatus of claim 17 wherein the inner surface of the vaporization plenum is substantially parallel to a line lying in the first direction.

30. A method for producing at high vaporization efficiency from a gas or vapor comprising a first substance and a vaporizable liquid comprising a second substance a flow of a low-temperature unsaturated gas-phase mixture of the first substance and vaporized second substance of substantially constant second substance concentration as a function of time, said method comprising:

(a) feeding the liquid comprising the second substance to the means of subparagraph (b) of claim 17;

(b) feeding the gas or vapor comprising the first substance to the means of subparagraph (c) of claim 17; and (c) operating the apparatus of claim 17 to produce the flow of a gas-phase mixture of the first substance and vaporized second substance of substantially constant second substance concentration as a function of time.

31. The method of claim 30 in which the temperature and amount of liquid comprising the second substance fed in step (a), the temperature and amount of gas or vapor comprising the first substance fed in step (b), and the operation of the apparatus are such that the gas-phase mixture of the first substance and vaporized second substance produced is low-temperature or unsaturated or both low-temperature and unsaturated.

32. The method of claim 30 in which the flow of the gas-phase mixture of the first substance and vaporized second substance is substantially continuous.

* * * * *